United States Patent
El Qacemi et al.

(10) Patent No.: US 9,456,606 B2
(45) Date of Patent: Oct. 4, 2016

(54) PESTICIDAL MIXTURES

(71) Applicant: Syngenta Participations AG, Basel (CH)

(72) Inventors: Myriem El Qacemi, Stein (CH); Jerome Yves Cassayre, Stein (CH)

(73) Assignee: Syngenta Participations AG, Basel (CH)

( * ) Notice: Subject to any disclaimer, the term of this patent is extended or adjusted under 35 U.S.C. 154(b) by 106 days.

(21) Appl. No.: 14/365,362

(22) PCT Filed: Dec. 12, 2012

(86) PCT No.: PCT/EP2012/075257
§ 371 (c)(1),
(2) Date: Jun. 13, 2014

(87) PCT Pub. No.: WO2013/087710
PCT Pub. Date: Jun. 20, 2013

(65) Prior Publication Data
US 2014/0371281 A1  Dec. 18, 2014

(30) Foreign Application Priority Data
Dec. 14, 2011  (EP) .................................... 11193506

(51) Int. Cl.
*A01N 43/80* (2006.01)
*A01N 43/36* (2006.01)
*A01N 37/38* (2006.01)
*A01N 43/38* (2006.01)

(52) U.S. Cl.
CPC ............. *A01N 43/80* (2013.01); *A01N 37/38* (2013.01); *A01N 43/36* (2013.01); *A01N 43/38* (2013.01)

(58) Field of Classification Search
None
See application file for complete search history.

(56) References Cited

U.S. PATENT DOCUMENTS

| 2011/0071141 A1 | 3/2011 | Murata et al. |
| 2011/0124858 A1* | 5/2011 | Iwata ..................... A01N 43/80 544/105 |

FOREIGN PATENT DOCUMENTS

| EP | 2186804 A1 | 5/2010 | |
| JP | WO 2009022746 A1 * | 2/2009 | ............ A01N 43/80 |
| JP | 2011178673 A | 9/2011 | |
| WO | 2010043315 A1 | 4/2010 | |
| WO | 2012060317 A1 | 5/2012 | |
| WO | 2012086462 A1 | 6/2012 | |

OTHER PUBLICATIONS

International Searh Report dated Sep. 24, 2013 for International Patent Application No. PCT/EP2012/075257.

* cited by examiner

*Primary Examiner* — Michael Barker
(74) *Attorney, Agent, or Firm* — R. Kody Jones

(57) ABSTRACT

The present invention relates to pesticidal mixtures comprising a component A and a component B, wherein component A is a compound of formula (I) wherein $B^1$, $B^2$, $B^3$, $X^1$, $X^2$, $X^3$, $X^4$, $Y^1$, $Y^2$, $Y^3$ and $R^9$ are as defined in claim 1 and component B is an insecticide. The present invention also relates to methods of using said mixtures for the control of plant pests.

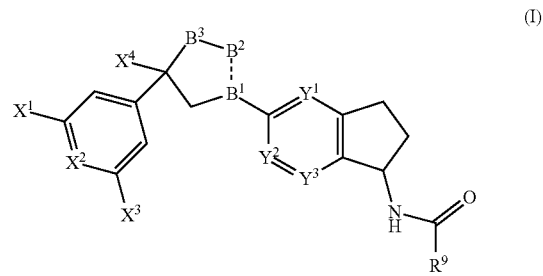

21 Claims, No Drawings

PESTICIDAL MIXTURES

RELATED APPLICATION INFORMATION

This application is a 371 of International Application No. PCT/EP2012/075257, filed 12 Dec. 2012, which claims priority to European Application No. 11193506.0, filed 14 Dec. 2011, the contents of which are incorporated herein by reference.

The present invention relates to mixtures of pesticidally active ingredients and to methods of using the mixtures in the field of agriculture.

The present invention provides pesticidal mixtures comprising a component A and a component B, wherein component A is a compound of formula I

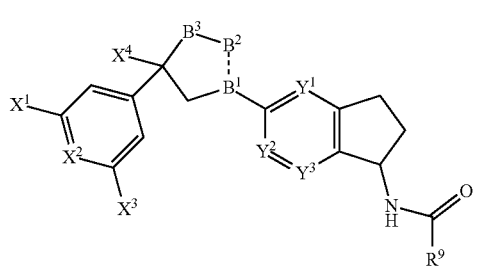

(I)

—$B^1$—$B^2$—$B^3$— is —C=N—O—, —C=N—$CH_2$— or —N—$CH_2$—$CH_2$—;
$Y^1$, $Y^2$ and $Y^3$ are independently CH or nitrogen;
wherein no more than two of $Y^1$, $Y^2$ and $Y^3$ are nitrogen and wherein $Y^2$ and $Y^3$ are not both nitrogen;
$R^9$ is $C_1$-$C_4$alkyl, $C_1$-$C_4$halo alkyl, $C_1$-$C_4$alkyl-O—$CH_2$—, $C_1$-$C_4$halo alkyl-O—$CH_2$—, $C_3$-$C_6$cyclo alkyl, $C_3$-$C_6$cycloalkyl-$CH_2$—, $C_1$-$C_4$alkyl-S—$CH_2$—, $C_1$-$C_4$alkyl-S(O)—$CH_2$—, $C_1$-$C_4$alkyl-S($O_2$)—$CH_2$;
$X^2$ is C—$X^6$ or nitrogen;
$X^1$, $X^3$ and $X^6$ are independently hydrogen, halogen or trihalomethyl, wherein at least two of
$X^1$, $X^3$ and $X^6$ are not hydrogen;
$X^4$ is trifluoromethyl, difluoromethyl or chlorodifluoromethyl;
and component B is a compound selected from
a) a pyrethroid including those selected from the group consisting of permethrin, cypermethrin, fenvalerate, esfenvalerate, deltamethrin, cyhalothrin, lambda-cyhalothrin, gamma-cyhalothrin, bifenthrin, fenpropathrin, cyfluthrin (including beta cyfluthrin), tefluthrin, ethofenprox, natural pyrethrin, tetramethrin, S-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;
b) an organophosphate including those selected from the group consisting of sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate and diazinon;
c) a carbamate including those selected from the group consisting of pirimicarb, triazamate, cloethocarb, carbofuran, furathiocarb, ethiofencarb, aldicarb, thiofurox, carbosulfan, bendiocarb, fenobucarb, propoxur, methomyl, thiodicarb and oxamyl;
d) a benzoyl urea including those selected from the group consisting of diflubenzuron, triflumuron, hexaflumuron, flufenoxuron, lufenuron and chlorfluazuron;
e) an organic tin compound selected from the group consisting of cyhexatin, fenbutatin oxide and azocyclotin;
f) a pyrazole including those selected from the group consisting of tebufenpyrad and fenpyroximate;
g) a macrolide including those selected from the group consisting of abamectin, emamectin (e.g. emamectin benzoate), ivermectin, milbemycin, spinosad, azadirachtin and spinetoram;
h) an organochlorine compound including those selected from the group consisting of endosulfan (in particular alpha-endosulfan), benzene hexachloride, DDT, chlordane and dieldrin;
i) an amidine including those selected from the group consisting of chlordimeform and amitraz;
j) a fumigant agent including those selected from the group consisting of chloropicrin, dichloropropane, methyl bromide and metam;
k) a neonicotinoid compound including those selected from the group consisting of imidacloprid, thiacloprid, acetamiprid, nitenpyram, dinotefuran, thiamethoxam, clothianidin, nithiazine and flonicamid;
l) a diacylhydrazine including those selected from the group consisting of tebufenozide, chromafenozide and methoxyfenozide;
m) a diphenyl ether including those selected from the group consisting of diofenolan and pyriproxyfen;
n) indoxacarb;
o) chlorfenapyr;
p) pymetrozine;
q) a tetramic acid compound including those selected from the group consisting of spirotetramat and spirodiclofen, or a tetronic acid compound including spiromesifen;
r) a diamide including those selected from the group consisting of flubendiamide, chlorantraniliprole (Rynaxypyr®) and cyantraniliprole;
s) sulfoxaflor;
t) metaflumizone;
u) fipronil and ethiprole;
v) pyrifluquinazon;
w) buprofezin;
x) diafenthiuron;
y) 4-[(6-Chloro-pyridin-3-ylmethyl)-(2,2-difluoro-ethyl)-amino]-5H-furan-2-one;
z) flupyradifurone.

Compounds in ground a)-z) are insecticidal compounds. In addition, component B may be a nematicidally active biological agent. The nematicidally active biological agent refers to any biological agent that has nematicidal activity. The biological agent can be any type known in the art including bacteria and fungi. The wording "nematicidally active" refers to having an effect on, such as reduction in damage caused by, agricultural-related nematodes. The nematicidally active biological agent can be a bacterium or a fungus. Preferably, the biological agent is a bacterium. Examples of nematicidally active bacteria include *Bacillus firmus, Bacillus cereus, Bacillus subtilis, P. nishizawae* and *Pasteuria penetrans*. A suitable *Bacillus firmus* strain is strain CNCM 1-1582 which is commercially available as BioNem™ A suitable *Bacillus cereus* strain is strain CNCM 1-1562. Of both *Bacillus* strains more details can be found in U.S. Pat. No. 6,406,690. Also of interest are *Streptomyces* spp. such as *S. avermitilis*, and fungi including *Metarhizium* spp. such as *M. anisopliae; Pochonia* spp. such as *P. chlamydosporia*.

Compounds of formula I are known to have insecticidal activity. Certain active ingredient mixtures of a compound of formula I and additional active ingredients can enhance the spectrum of action with respect to the pest to be controlled, For example, the combination of A and B may cause an increase in the expected insecticidal action. This allows, on the one hand, a substantial broadening of the spectrum of pests that can be controlled and, on the other hand, increased safety in use through lower rates of application.

However, besides the actual synergistic action with respect to pest control, the pesticidal compositions according to the invention can have further surprising advantageous properties which can also be described, in a wider sense, as synergistic activity. Examples of such advantageous properties that may be mentioned are: a broadening of the spectrum of pest control to other pests, for example to resistant strains; a reduction in the rate of application of the active ingredients; adequate pest control with the aid of the compositions according to the invention, even at a rate of application at which the individual compounds are totally ineffective; advantageous behaviour during formulation and/or upon application, for example upon grinding, sieving, emulsifying, dissolving or dispensing; increased storage stability; improved stability to light; more advantageuos degradability; improved toxicological and/or ecotoxicological behaviour; improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination; or any other advantages familiar to a person skilled in the art.

Compounds of formula I may be prepared according to the methods described in WO2009/112275, WO2011/141414, WO2010/043315, WO11051455. The components B are known, e.g. from "The Pesticide Manual", Fifteenth Edition, Edited by Clive Tomlin, British Crop Protection Council.

The combinations according to the invention may also comprise more than one of the active components B, if, for example, a broadening of the spectrum of pest control is desired. For instance, it may be advantageous in the agricultural practice to combine two or three components B with any of the compounds of formula I, or with any preferred member of the group of compounds of formula I. The mixtures of the invention may also comprise other active ingredients in addition to components A and B. In other embodiments the mixtures of the invention may include only components A and B as pesticidally active ingredients, e.g. no more than two pesticidally active ingredients.

The compounds of formula (I) may exist in different geometric or optical isomers or tautomeric forms. This invention covers all such isomers and tautomers and mixtures thereof in all proportions as well as isotopic forms such as deuterated compounds. The invention also covers salts and N-oxides of the compounds of the invention.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Halogen is fluorine, chlorine, bromine or iodine.

Haloalkyl groups are alkyl groups which are substituted by one or more of the same or different halogen atoms and are, for example, difluoromethyl, trifluoromethyl, chlorodifluoromethyl or 2,2,2-trifluoro-ethyl.

Preferred substituent definitions are described below and may be combined in any combination, including with original definitions.

Preferably $R^9$ is $C_1$-$C_4$alkyl, $C_1$-$C_4$haloalkyl, $C_1$-$C_4$alkyl-O—$CH_2$—, $C_1$-$C_4$haloalkyl-O—$CH_2$—, $C_3$-$C_6$cycloalkyl, $C_3$-$C_6$cycloalkyl-$CH_2$—, $C_1$-$C_4$alkyl-S(O)—$CH_2$—, $C_1$-$C_4$alkyl-S($O_2$)—$CH_2$—, more preferably $C_1$-$C_4$alkyl, $C_1$-$C_4$haloalkyl, $C_1$-$C_4$alkyl-O—$CH_2$—, $C_1$-$C_4$haloalkyl-O—$CH_2$—, $C_3$-$C_6$cycloalkyl, $C_3$-$C_6$cycloalkyl-$CH_2$—, more preferably $C_1$-$C_4$alkyl, $C_1$-$C_4$haloalkyl or $C_3$-$C_4$cycloalkyl, more preferably methyl, ethyl, propyl, $CF_3CH_2$— or cyclopropyl, even more preferably ethyl, —$CH_2CF_3$ or cyclopropyl, even more preferably ethyl or —$CH_2CF_3$, most preferably ethyl.

Preferably $Y^1$ is CH, $Y^2$ is CH, $Y^3$ is CH, or $Y^1$ is N, $Y^2$ is CH, $Y^3$ is CH, or $Y^1$ is N, $Y^2$ is N, $Y^3$ is CH, or $Y^1$ is CH, $Y^2$ is N, $Y^3$ is CH, or $Y^1$ is CH, $Y^2$ is CH, $Y^3$ is N. Preferably $Y^1$ is CH, $Y^2$ is CH and $Y^3$ is CH.

Preferably $X^2$ is C—$X^6$;

Preferably $X^1$, $X^3$ and $X^6$ are independently hydrogen, halogen or trifluoromethyl, wherein at least two of $X^1$, $X^3$ and $X^6$ are not hydrogen. More preferably $X^1$, $X^3$ and $X^6$ are independently hydrogen, chloro, bromo or trifluoromethyl, wherein at least two of $X^1$, $X^3$ and $X^6$ are not hydrogen. Preferably at least two of $X^1$, $X^3$ and $X^6$ are (independently) chloro, bromo or trifluoromethyl.

For example $X^1$ is chloro, $X^2$ is CH, $X^3$ is chloro, or $X^1$ is chloro, $X^2$ is C—F, $X^3$ is hydrogen, or $X^1$ is fluoro, $X^2$ is C—Cl, $X^3$ is hydrogen, or $X^1$ is chloro, $X^2$ is C—Cl, $X^3$ is hydrogen, or $X^1$ is chloro, $X^2$ is C—Br, $X^3$ is chloro, or $X^1$ is chloro, $X^2$ is C—F, $X^3$ is chloro, or $X^1$ is chloro, $X^2$ is C—Cl, $X^3$ is chloro, or $X^1$ is chloro, $X^2$ is C—I, $X^3$ is chloro, or $X^1$ is fluoro, $X^2$ is C—F, $X^3$ is fluoro, or $X^1$ is chloro, $X^2$ is CH, $X^3$ is bromo, or $X^1$ is chloro, $X^2$ is CH, $X^3$ is fluoro, or $X^1$ is chloro, $X^2$ is CH, $X^3$ is trifluoromethyl, or $X^1$ is bromo, $X^2$ is CH, $X^3$ is trifluoromethyl, or $X^1$ is chloro, $X^2$ is C—Cl, $X^3$ is trifluoromethyl, or $X^1$ is trifluoromethyl, $X^2$ is CH, $X^3$ is trifluoromethyl, or $X^1$ is trifluoromethyl, $X^2$ is C—Cl, $X^3$ is trifluoromethyl, or $X^1$ is trifluoromethyl, $X^2$ is CH, $X^3$ is hydrogen, or $X^1$ is chloro, $X^2$ is N, $X^3$ is chloro, or $X^1$ is trifluoromethyl, $X^2$ is N, $X^3$ is trifluoromethyl. More preferably $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro, or $X^1$ is chloro, $X^2$ is CH, $X^3$ is trifluoromethyl, or $X^1$ is chloro, $X^2$ is C—F, $X^3$ is chloro, most preferably $X^1$ is chloro, $X^2$ is CH, $X^3$ is chloro.

Preferably $X^4$ is trifluoromethyl, or chlorodifluoromethyl, more preferably trifluoromethyl.

In one preferred group of compounds —$B^1$—$B^2$—$B^3$— is —C=N—O—.

In another group of compounds —$B^1$—$B^2$—$B^3$— is —C=N—$CH_2$—.

In another group of compounds —$B^1$—$B^2$—$B^3$— is —N—$CH_2$—$CH_2$—.

In another group of compounds —$B^1$—$B^2$—$B^3$— is —C=N—$CH_2$— or —N—$CH_2$—$CH_2$—.

In another group of compounds $X^2$ is C—$X^6$, $Y^1$, $Y^2$ and $Y^3$ are CH.

In another group of compounds —$B^1$—$B^2$—$B^3$— is —C=N—$CH_2$—, $X^2$ is C—$X^6$, $Y^1$, $Y^2$, and $Y^3$ are CH and $R^9$ is $C_1$-$C_4$alkyl, $C_1$-$C_4$haloalkyl or $C_3$-$C_4$cycloalkyl.

In another group of compounds —$B^1$—$B^2$—$B^3$— is —C=N—$CH_2$—, $X^2$ is C—$X^6$, $Y^1$, $Y^2$, and $Y^3$ are CH, $R^9$ is ethyl, cyclopropyl or —$CH_2CF_3$.

In another group of compounds —$B^1$—$B^2$—$B^3$— is —C=N—$CH_2$—, $X^2$ is C—$X^6$, $Y^1$, $Y^2$ and $Y^3$ are CH, $R^9$ is $C_1$-$C_4$alkyl, $C_1$-$C_4$haloalkyl or $C_3$-$C_4$cycloalkyl, $X^4$ is trifluoromethyl.

In another group of compounds —$B^1$—$B^2$—$B^3$— is —C=N—$CH_2$—, $X^2$ is C—$X^6$, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl.

In another group of compounds —$B^1$—$B^2$—$B^3$— is —C=N—$CH_2$—, $Y^1$, $Y^2$, and $Y^3$ are CH and $R^9$ is ethyl, cyclopropyl or —$CH_2CF_3$, preferably ethyl or —$CH_2CF_3$, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another group of compounds —$B^1$—$B^2$—$B^3$— is —C=N—$CH_2$—, $Y^1$, $Y^2$, and $Y^3$ are CH and $R^9$ is ethyl, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another group of compounds —$B^1$—$B^2$—$B^3$— is —C=N—$CH_2$—, $Y^1$, $Y^2$, and $Y^3$ are CH and $R^9$ is —$CH_2CF_3$, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another group of compounds —$B^1$—$B^2$—$B^3$— is —C=N—$CH_2$—, $Y^1$, $Y^2$, and $Y^3$ are CH and $R^9$ is cyclopropyl, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another group of compounds —$B^1$—$B^2$—$B^3$— is —C=N—$CH_2$—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is CH, $X^3$ is chloro.

In another group of compounds —$B^1$—$B^2$—$B^3$— is —C=N—$CH_2$—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is C—Cl, $X^3$ is chloro.

In another group of compounds —$B^1$—$B^2$—$B^3$— is —C=N—$CH_2$—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is trifluoromethyl, $X^2$ is CH, $X^3$ is trifluoromethyl.

In another group of compounds —$B^1$—$B^2$—$B^3$— is —C=N—$CH_2$—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is CH, $X^3$ is trifluoromethyl.

In another group of compounds —$B^1$—$B^2$—$B^3$— is —C=N—$CH_2$—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is C—F, $X^3$ is chloro.

In another group of compounds —$B^1$—$B^2$—$B^3$— is —C=N—$CH_2$—, $Y^1$, $Y^2$, and $Y^3$ are CH, $R^9$ is ethyl and $X^1$ is chloro, $X^2$ is CH, $X^3$ is chloro or $X^1$ is chloro, $X^2$ is C—Cl, $X^3$ is chloro or $X^1$ is trifluoromethyl, $X^2$ is CH, $X^3$ is trifluoromethyl.

In another group of compounds —$B^1$—$B^2$—$B^3$— is —C=N—$CH_2$—, $Y^1$, $Y^2$, and $Y^3$ are CH, $R^9$ is cyclopropyl and $X^1$ is chloro, $X^2$ is C—H, $X^3$ is chloro or $X^1$ is chloro, $X^2$ is C—Cl, $X^3$ is chloro or $X^1$ is trifluoromethyl, $X^2$ is CH, $X^3$ is trifluoromethyl.

In another group of compounds —$B^1$—$B^2$—$B^3$— is —C=N—$CH_2$—, $Y^1$, $Y^2$, and $Y^3$ are CH, $R^9$ is —$CH_2CF_3$ and $X^1$ is chloro, $X^2$ is CH, $X^3$ is chloro or $X^1$ is chloro, $X^2$ is C—Cl, $X^3$ is chloro or $X^1$ is trifluoromethyl, $X^2$ is CH, $X^3$ is trifluoromethyl.

In another group of compounds —$B^1$—$B^2$—$B^3$— is —N—$CH_2$—$CH_2$—, $X^2$ is C—$X^6$, $Y^1$, $Y^2$, and $Y^3$ are CH and $R^9$ is $C_1$-$C_4$alkyl, $C_1$-$C_4$haloalkyl or $C_3$-$C_4$cycloalkyl.

In another group of compounds —$B^1$—$B^2$—$B^3$— is —N—$CH_2$—$CH_2$—, $X^2$ is C—$X^6$, $Y^1$, $Y^2$ and $Y^3$ are CH, $R^9$ is ethyl, cyclopropyl or —$CH_2CF_3$.

In another group of compounds —$B^1$—$B^2$—$B^3$— is —N—$CH_2$—$CH_2$—, $X^2$ is C—$X^6$, $Y^1$, $Y^2$ and $Y^3$ are CH, $R^9$ is $C_1$-$C_4$alkyl, $C_1$-$C_4$haloalkyl or $C_3$-$C_4$cycloalkyl, $X^4$ is trifluoromethyl.

In another group of compounds —$B^1$—$B^2$—$B^3$— is —N—$CH_2$—$CH_2$—, $X^2$ is C—$X^6$, $Y^1$, $Y^2$ and $Y^3$ are CH, $R^9$ is ethyl, cyclopropyl or —$CH_2CF_3$, $X^4$ is trifluoromethyl.

In another group of compounds —$B^1$—$B^2$—$B^3$— is —N—$CH_2$—$CH_2$—, $Y^1$, $Y^2$, and $Y^3$ are CH and $R^9$ is ethyl, cyclopropyl or —$CH_2CF_3$, preferably ethyl or —$CH_2CF_3$, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another group of compounds —$B^1$—$B^2$—$B^3$— is —N—$CH_2$—$CH_2$—, $Y^1$, $Y^2$, and $Y^3$ are CH and $R^9$ is ethyl, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another group of compounds —$B^1$—$B^2$—$B^3$— is —N—$CH_2$—$CH_2$—, $Y^1$, $Y^2$, and $Y^3$ are CH and $R^9$ is —$CH_2CF_3$, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another group of compounds —$B^1$—$B^2$—$B^3$— is —N—$CH_2$—$CH_2$—, $Y^1$, $Y^2$, and $Y^3$ are CH and $R^9$ is cyclopropyl, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another group of compounds —$B^1$—$B^2$—$B^3$— is —N—$CH_2$—$CH_2$—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is CH, $X^3$ is chloro.

In another group of compounds —$B^1$—$B^2$—$B^3$— is —N—$CH_2$—$CH_2$—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is C—Cl, $X^3$ is chloro.

In another group of compounds —$B^1$—$B^2$—$B^3$— is —N—$CH_2$—$CH_2$—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is trifluoromethyl, $X^2$ is CH, $X^3$ is trifluoromethyl.

In another group of compounds —$B^1$—$B^2$—$B^3$— is —N—$CH_2$—$CH_2$—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is CH, $X^3$ is trifluoromethyl.

In another group of compounds —$B^1$—$B^2$—$B^3$— is —N—$CH_2$—$CH_2$—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is C—F, $X^3$ is chloro.

In another group of compounds —$B^1$—$B^2$—$B^3$— is —N—$CH_2$—$CH_2$—, $Y^1$, $Y^2$, and $Y^3$ are CH, $R^9$ is ethyl and $X^1$ is chloro, $X^2$ is CH, $X^3$ is chloro or $X^1$ is chloro, $X^2$ is C—Cl, $X^3$ is chloro or $X^1$ is trifluoromethyl, $X^2$ is CH, $X^3$ is trifluoromethyl.

In another group of compounds —$B^1$—$B^2$—$B^3$— is —N—$CH_2$—$CH_2$—, $Y^1$, $Y^2$, and $Y^3$ are CH, $R^9$ is cyclopropyl and $X^1$ is chloro, $X^2$ is CH, $X^3$ is chloro or $X^1$ is chloro, $X^2$ is C—Cl, $X^3$ is chloro or $X^1$ is trifluoromethyl, $X^2$ is CH, $X^3$ is trifluoromethyl.

In another group of compounds —$B^1$—$B^2$—$B^3$— is —N—$CH_2$—$CH_2$— $Y^1$, $Y^2$, and $Y^3$ are CH, $R^9$ is —$CH_2CF_3$ and $X^1$ is chloro, $X^2$ is CH, $X^3$ is chloro or $X^1$ is chloro, $X^2$ is C—Cl, $X^3$ is chloro or $X^1$ is trifluoromethyl, $X^2$ is CH, $X^3$ is trifluoromethyl.

In a preferred group of compounds —$B^1$—$B^2$—$B^3$— is —C=N—O—, $X^2$ is C—$X^6$, $Y^1$, $Y^2$, and $Y^3$ are CH and $R^9$ is $C_1$-$C_4$alkyl, $C_1$-$C_4$haloalkyl or $C_3$-$C_4$cycloalkyl.

In another preferred group of compounds —$B^1$—$B^2$—$B^3$— is —C=N—O—, $X^2$ is C—$X^6$, $Y^1$, $Y^2$, and $Y^3$ are CH, $R^9$ is ethyl, cyclopropyl or —$CH_2CF_3$, preferably ethyl or —$CH_2CF_3$.

In a more preferred group of compounds —$B^1$—$B^2$—$B^3$— is —C=N—O—, $X^2$ is C—$X^6$, $Y^1$, $Y^2$ and $Y^3$ are CH, $R^9$ is $C_1$-$C_4$alkyl, $C_1$-$C_4$haloalkyl or $C_3$-$C_4$cycloalkyl, preferably ethyl or —$CH_2CF_3$, $X^4$ is trifluoromethyl.

In another more preferred group of compounds —$B^1$—$B^2$—$B^3$— is —C=N—O—, $X^2$ is C—$X^6$, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl.

In a very preferred group of compounds —$B^1$—$B^2$—$B^3$— is —C=N—O—, $Y^1$, $Y^2$, and $Y^3$ are CH and $R^9$ is ethyl, cyclopropyl or —$CH_2CF_3$, preferably ethyl or —$CH_2CF_3$, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another very preferred group of compounds —$B^1$—$B^2$—$B^3$— is —C=N—O—, $Y^1$, $Y^2$ and $Y^3$ are CH and $R^9$ is ethyl, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another very preferred group of compounds —$B^1$—$B^2$—$B^3$— is —C=N—O—, $Y^1$, $Y^2$ and $Y^3$ are CH and $R^9$ is —$CH_2CF_3$, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another very preferred group of compounds —$B^1$—$B^2$—$B^3$— is —C=N—O—, $Y^1$, $Y^2$, and $Y^3$ are CH and $R^9$ is cyclopropyl, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another very preferred group of compounds —$B^1$—$B^2$—$B^3$— is —C=N—O—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is CH, $X^3$ is chloro.

In another very preferred group of compounds —$B^1$—$B^2$—$B^3$— is —C=N—O—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is C—Cl, $X^3$ is chloro.

In another very preferred group of compounds —$B^1$—$B^2$—$B^3$— is —C=N—O—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is trifluoromethyl, $X^2$ is CH, $X^3$ is trifluoromethyl.

In another very preferred group of compounds —$B^1$—$B^2$—$B^3$— is —C=N—O—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is CH, $X^3$ is trifluoromethyl.

In another very preferred group of compounds —$B^1$—$B^2$—$B^3$— is —C=N—O—, $Y^1$, $Y^2$ and $Y^3$ are CH, $R^9$ is ethyl, cyclopropyl or —$CH_2CF_3$, preferably ethyl or —$CH_2CF_3$, $X^4$ is trifluoromethyl, $X^1$ is chloro, $X^2$ is C—F, $X^3$ is chloro.

In another very preferred group of compounds —$B^1$—$B^2$—$B^3$— is —C=N—O—, $Y^1$, $Y^2$, and $Y^3$ are CH, $R^9$ is ethyl and $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another very preferred group of compounds —$B^1$—$B^2$—$B^3$— is —C=N—O—, $Y^1$, $Y^2$, and $Y^3$ are CH, $R^9$ is cyclopropyl and $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another very preferred group of compounds —$B^1$—$B^2$—$B^3$— is —C=N—O—, $Y^1$, $Y^2$, and $Y^3$ are CH, $R^9$ is —$CH_2CF_3$ and $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another very preferred group of compounds —$B^1$—$B^2$—$B^3$— is —C=N—O—, $Y^1$, $Y^2$ and $Y^3$ are CH, $R^9$ is ethyl, $X^4$ is trifluoromethyl and $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another very preferred group of compounds —$B^1$—$B^2$—$B^3$— is —C=N—O—, $Y^1$, $Y^2$ and $Y^3$ are CH, $R^9$ is cyclopropyl, $X^4$ is trifluoromethyl and $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another very preferred group of compounds —$B^1$—$B^2$—$B^3$— is —C=N—O—, $Y^1$, $Y^2$ and $Y^3$ are CH, $R^9$ is —$CH_2CF_3$, $X^4$ is trifluoromethyl and $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro or $X^1$ is chloro, $X^2$ is CH, $X^3$ is trifluoromethyl, or $X^1$ is chloro, $X^2$ is C—F, $X^3$ is chloro.

In another group of compounds —$B^1$—$B^2$—$B^3$— is —C=N—O—, $X^2$ is C—$X^6$, $Y^1$, $Y^2$, and $Y^3$ are C—H, $R^9$ is ethyl and $X^1$ is chloro, $X^2$ is C—Cl, $X^3$ is chloro or $X^1$ is chloro, $X^2$ is C—Cl, $X^3$ is chloro or $X^1$ is trifluoromethyl, $X^2$ is CH, $X^3$ is trifluoromethyl.

In another group of compounds —$B^1$—$B^2$—$B^3$— is —C=N—O—, $X^2$ is C—$X^6$, $Y^1$, $Y^2$, and $Y^3$ are C—H, $R^9$ is cyclopropyl and $X^1$ is chloro, $X^2$ is C—Cl, $X^3$ is chloro or $X^1$ is chloro, $X^2$ is C—Cl, $X^3$ is chloro or $X^1$ is trifluoromethyl, $X^2$ is CH, $X^3$ is trifluoromethyl.

In another group of compounds —$B^1$—$B^2$—$B^3$— is —C=N—O—, $X^2$ is C—$X^6$, $Y^1$, $Y^2$, and $Y^3$ are C—H, $R^9$ is —$CH_2CF_3$ and $X^1$ is chloro, $X^2$ is C—Cl, $X^3$ is chloro or $X^1$ is chloro, $X^2$ is C—Cl, $X^3$ is chloro or $X^1$ is trifluoromethyl, $X^2$ is CH, $X^3$ is trifluoromethyl.

Due to a stereocenter, compounds of formula I include may exist as compounds of formula I* or compounds of formula I**.

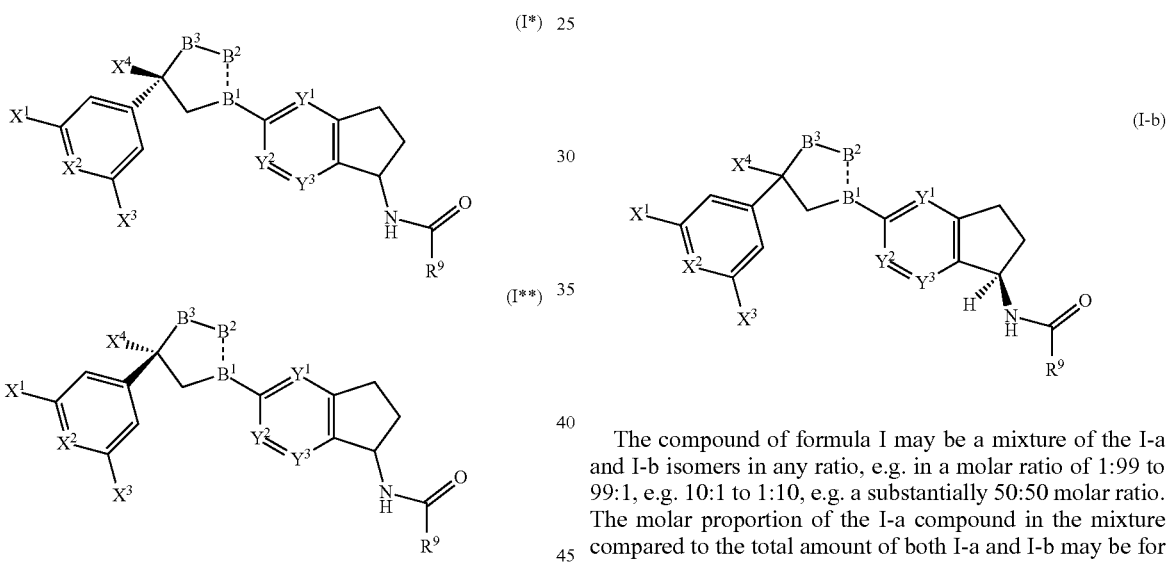

Compounds of formula I** are more biologically active than compounds of formula I* and are preferred. The compound of formula I may be a mixture of compounds I* and I in any ratio e.g. in a molar ratio of 1:99 to 99:1, e.g. 10:1 to 1:10, e.g. a substantially 50:50 molar ratio. Preferably the compound of formula I is a racemic mixture of the compounds of formula I and I* or is enantiomerically enriched for the compound of formula I. For example, when the compound of formula I is an enantiomerically enriched mixture of formula I, the molar proportion of compound I compared to the total amount of both enantiomers is for example greater than 50%, e.g. at least 55, 60, 65, 70, 75, 80, 85, 90, 95, 96, 97, 98, or at least 99%. Preferably the compound of formula I is at least 90% enriched for the compound of formula I.

In one embodiment component A is a compound of formula I in substantially pure form, e.g. it is provided substantially in the absence of the alternative enantiomer. Enantio-enriched mixtures of the invention do not contain any compounds of formula I in addition to component A. In other words, the molar amount of compound of formula I in the enantio-enriched mixtures of the invention is greater than the molar amount of the compounds of formula I*.

The invention also provides mixtures consisting of component A and component B in addition to customary formulation ingredients, e.g. an agriculturally acceptable carrier and optionally a surfactant.

Due to an additional chiral centre compounds of formula I may exist as compounds of formula I-a or I-b

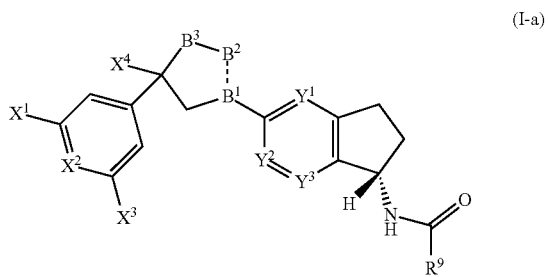

The compound of formula I may be a mixture of the I-a and I-b isomers in any ratio, e.g. in a molar ratio of 1:99 to 99:1, e.g. 10:1 to 1:10, e.g. a substantially 50:50 molar ratio. The molar proportion of the I-a compound in the mixture compared to the total amount of both I-a and I-b may be for example greater than 50%, e.g. at least 55, 60, 65, 70, 75, 80, 85, 90, 95, 96, 97, 98, or at least 99%. The molar proportion of the I-a compound in the mixture compared to the total amount of both I-a and I-b may be for example greater than 50%, e.g. at least 55, 60, 65, 70, 75, 80, 85, 90, 95, 96, 97, 98, or at least 99%.

Thus compounds of formula I may exist as compounds of formula I*-a, I**-a, I*-b and I**-b

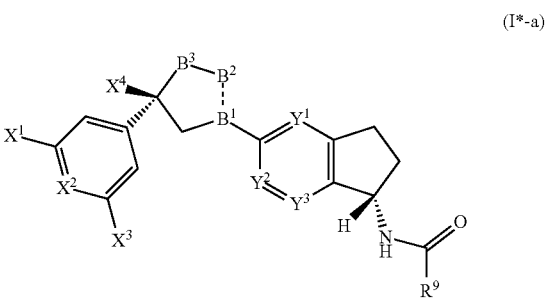

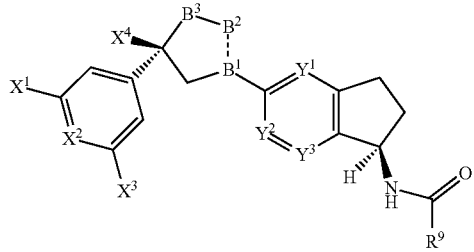

(I*-b)

(I**-a)

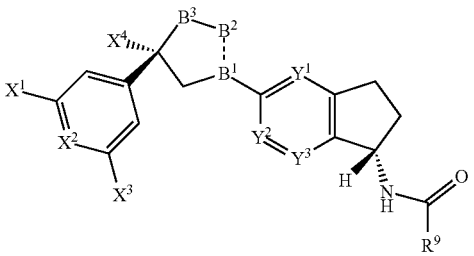

(I**-b)

The mixtures of the invention may, if desired, be enriched for the compound of formula I-a or Ib. When the compound of formula I is an enantiomerically enriched mixture of formula I-b, the molar proportion of compound I-b compared to the total amount of the four enantiomers is for example greater than 25%, e.g. at least 30, 35, 40, 45, 50, 55, 60, 65, 70, 75, 80, 85, 90, 95, 96, 97, 98, or at least 99%. When the compound of formula I is an enantiomerically enriched mixture of formula I-a, the molar proportion of compound I-a compared to the total amount of the four enantiomers is for example greater than 25%, e.g. at least 30, 35, 40, 45, 50, 55, 60, 65, 70, 75, 80, 85, 90, 95, 96, 97, 98, or at least 99%.

A selection of preferred compounds of formula I are the compounds depicted in the tables below. The symbol * indicates the location of the chiral centre. I refers to a compound of formula I.

TABLE A

Compounds of formula Ia

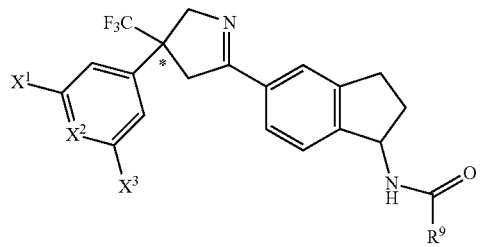

(Ia)

| Comp No. | Stereochemistry at * | X1 | X2 | X3 | R$^9$ |
|---|---|---|---|---|---|
| 1 | racemic mixture | Cl | C—Cl | Cl | methyl |
| 2 | racemic mixture | Cl | C—Cl | Cl | ethyl |
| 3 | racemic mixture | Cl | C—Cl | Cl | cyclopropyl |
| 4 | racemic mixture | Cl | C—Cl | Cl | CF$_3$CH$_2$— |
| 5 | racemic mixture | Cl | C—Cl | Cl | cyclopropyl-CH$_2$— |
| 6 | racemic mixture | Cl | C—Cl | Cl | isopropyl |
| 7 | racemic mixture | Cl | C—H | Cl | methyl |
| 8 | racemic mixture | Cl | C—H | Cl | ethyl |
| 9 | racemic mixture | Cl | C—H | Cl | cyclopropyl |
| 10 | racemic mixture | Cl | C—H | Cl | CF$_3$CH$_2$— |
| 11 | racemic mixture | Cl | C—H | Cl | cyclopropyl-CH$_2$— |
| 12 | racemic mixture | Cl | C—H | Cl | isopropyl |
| 13 | racemic mixture | CF$_3$ | C—H | CF$_3$ | methyl |
| 14 | racemic mixture | CF$_3$ | C—H | CF$_3$ | ethyl |
| 15 | racemic mixture | CF$_3$ | C—H | CF$_3$ | cyclopropyl |
| 16 | racemic mixture | CF$_3$ | C—H | CF$_3$ | CF$_3$CH$_2$— |
| 17 | racemic mixture | CF$_3$ | C—H | CF$_3$ | cyclopropyl-CH$_2$— |
| 18 | racemic mixture | CF$_3$ | C—H | CF$_3$ | isopropyl |
| 19 | racemic mixture | Cl | C—H | CF$_3$ | methyl |
| 20 | racemic mixture | Cl | C—H | CF$_3$ | ethyl |
| 21 | racemic mixture | Cl | C—H | CF$_3$ | cyclopropyl |
| 22 | racemic mixture | Cl | C—H | CF$_3$ | CF$_3$CH$_2$— |
| 23 | racemic mixture | Cl | C—H | CF$_3$ | cyclopropyl-CH$_2$— |
| 24 | racemic mixture | Cl | C—H | CF$_3$ | isopropyl |
| 25 | racemic mixture | Br | C—H | CF$_3$ | methyl |
| 26 | racemic mixture | Br | C—H | CF$_3$ | ethyl |
| 27 | racemic mixture | Br | C—H | CF$_3$ | cyclopropyl |
| 28 | racemic mixture | Br | C—H | CF$_3$ | CF$_3$CH$_2$— |
| 29 | racemic mixture | Br | C—H | CF$_3$ | cyclopropyl-CH$_2$— |
| 30 | racemic mixture | Br | C—H | CF$_3$ | isopropyl |
| 31 | as for I** | Cl | C—Cl | Cl | methyl |
| 32 | as for I** | Cl | C—Cl | Cl | ethyl |
| 33 | as for I** | Cl | C—Cl | Cl | cyclopropyl |
| 34 | as for I** | Cl | C—Cl | Cl | CF$_3$CH$_2$— |
| 35 | as for I** | Cl | C—Cl | Cl | cyclopropyl-CH$_2$— |
| 36 | as for I** | Cl | C—Cl | Cl | isopropyl |
| 37 | as for I** | Cl | C—H | Cl | methyl |
| 38 | as for I** | Cl | C—H | Cl | ethyl |
| 39 | as for I** | Cl | C—H | Cl | cyclopropyl |
| 40 | as for I** | Cl | C—H | Cl | CF$_3$CH$_2$— |
| 41 | as for I** | Cl | C—H | Cl | cyclopropyl-CH$_2$— |
| 42 | as for I** | Cl | C—H | Cl | isopropyl |
| 43 | as for I** | CF$_3$ | C—H | CF$_3$ | methyl |
| 44 | as for I** | CF$_3$ | C—H | CF$_3$ | ethyl |
| 45 | as for I** | CF$_3$ | C—H | CF$_3$ | cyclopropyl |
| 46 | as for I** | CF$_3$ | C—H | CF$_3$ | CF$_3$CH$_2$— |
| 47 | as for I** | CF$_3$ | C—H | CF$_3$ | cyclopropyl-CH$_2$— |
| 48 | as for I** | CF$_3$ | C—H | CF$_3$ | isopropyl |
| 49 | as for I** | Cl | C—H | CF$_3$ | methyl |
| 50 | as for I** | Cl | C—H | CF$_3$ | ethyl |
| 51 | as for I** | Cl | C—H | CF$_3$ | cyclopropyl |
| 52 | as for I** | Cl | C—H | CF$_3$ | CF$_3$CH$_2$— |
| 53 | as for I** | Cl | C—H | CF$_3$ | cyclopropyl-CH$_2$— |
| 54 | as for I** | Cl | C—H | CF$_3$ | isopropyl |
| 55 | as for I** | Br | C—H | CF$_3$ | methyl |
| 56 | as for I** | Br | C—H | CF$_3$ | ethyl |
| 57 | as for I** | Br | C—H | CF$_3$ | cyclopropyl |
| 58 | as for I** | Br | C—H | CF$_3$ | CF$_3$CH$_2$— |
| 59 | as for I** | Br | C—H | CF$_3$ | cyclopropyl-CH$_2$— |
| 60 | as for I** | Br | C—H | CF$_3$ | isopropyl |

TABLE B

Compounds of formula Ib (Ib)

| Comp No. | Stereochemistry at * | X1 | X2 | X3 | R⁹ |
|---|---|---|---|---|---|
| 1 | racemic mixture | Cl | C—Cl | Cl | methyl |
| 2 | racemic mixture | Cl | C—Cl | Cl | ethyl |
| 3 | racemic mixture | Cl | C—Cl | Cl | cyclopropyl |
| 4 | racemic mixture | Cl | C—Cl | Cl | $CF_3CH_2$— |
| 5 | racemic mixture | Cl | C—Cl | Cl | cyclopropyl-$CH_2$— |
| 6 | racemic mixture | Cl | C—Cl | Cl | isopropyl |
| 7 | racemic mixture | Cl | C—H | Cl | methyl |
| 8 | racemic mixture | Cl | C—H | Cl | ethyl |
| 9 | racemic mixture | Cl | C—H | Cl | cyclopropyl |
| 10 | racemic mixture | Cl | C—H | Cl | $CF_3CH_2$— |
| 11 | racemic mixture | Cl | C—H | Cl | cyclopropyl-$CH_2$— |
| 12 | racemic mixture | Cl | C—H | Cl | isopropyl |
| 13 | racemic mixture | $CF_3$ | C—H | $CF_3$ | methyl |
| 14 | racemic mixture | $CF_3$ | C—H | $CF_3$ | ethyl |
| 15 | racemic mixture | $CF_3$ | C—H | $CF_3$ | cyclopropyl |
| 16 | racemic mixture | $CF_3$ | C—H | $CF_3$ | $CF_3CH_2$— |
| 17 | racemic mixture | $CF_3$ | C—H | $CF_3$ | cyclopropyl-$CH_2$— |
| 18 | racemic mixture | $CF_3$ | C—H | $CF_3$ | isopropyl |
| 19 | racemic mixture | Cl | C—H | $CF_3$ | methyl |
| 20 | racemic mixture | Cl | C—H | $CF_3$ | ethyl |
| 21 | racemic mixture | Cl | C—H | $CF_3$ | cyclopropyl |
| 22 | racemic mixture | Cl | C—H | $CF_3$ | $CF_3CH_2$— |
| 23 | racemic mixture | Cl | C—H | $CF_3$ | cyclopropyl-$CH_2$— |
| 24 | racemic mixture | Cl | C—H | $CF_3$ | isopropyl |
| 25 | racemic mixture | Br | C—H | $CF_3$ | methyl |
| 26 | racemic mixture | Br | C—H | $CF_3$ | ethyl |
| 27 | racemic mixture | Br | C—H | $CF_3$ | cyclopropyl |
| 28 | racemic mixture | Br | C—H | $CF_3$ | $CF_3CH_2$— |
| 29 | racemic mixture | Br | C—H | $CF_3$ | cyclopropyl-$CH_2$— |
| 30 | racemic mixture | Br | C—H | $CF_3$ | isopropyl |
| 31 | as for I** | Cl | C—Cl | Cl | methyl |
| 32 | as for I** | Cl | C—Cl | Cl | ethyl |
| 33 | as for I** | Cl | C—Cl | Cl | cyclopropyl |
| 34 | as for I** | Cl | C—Cl | Cl | $CF_3CH_2$— |
| 35 | as for I** | Cl | C—Cl | Cl | cyclopropyl-$CH_2$— |
| 36 | as for I** | Cl | C—Cl | Cl | isopropyl |
| 37 | as for I** | Cl | C—H | Cl | methyl |
| 38 | as for I** | Cl | C—H | Cl | ethyl |
| 39 | as for I** | Cl | C—H | Cl | cyclopropyl |
| 40 | as for I** | Cl | C—H | Cl | $CF_3CH_2$— |
| 41 | as for I** | Cl | C—H | Cl | cyclopropyl-$CH_2$— |
| 42 | as for I** | Cl | C—H | Cl | isopropyl |
| 43 | as for I** | $CF_3$ | C—H | $CF_3$ | methyl |
| 44 | as for I** | $CF_3$ | C—H | $CF_3$ | ethyl |
| 45 | as for I** | $CF_3$ | C—H | $CF_3$ | cyclopropyl |
| 46 | as for I** | $CF_3$ | C—H | $CF_3$ | $CF_3CH_2$— |
| 47 | as for I** | $CF_3$ | C—H | $CF_3$ | cyclopropyl-$CH_2$— |
| 48 | as for I** | $CF_3$ | C—H | $CF_3$ | isopropyl |
| 49 | as for I** | Cl | C—H | $CF_3$ | methyl |
| 50 | as for I** | Cl | C—H | $CF_3$ | ethyl |
| 51 | as for I** | Cl | C—H | $CF_3$ | cyclopropyl |
| 52 | as for I** | Cl | C—H | $CF_3$ | $CF_3CH_2$— |
| 53 | as for I** | Cl | C—H | $CF_3$ | cyclopropyl-$CH_2$— |
| 54 | as for I** | Cl | C—H | $CF_3$ | isopropyl |
| 55 | as for I** | Br | C—H | $CF_3$ | methyl |
| 56 | as for I** | Br | C—H | $CF_3$ | ethyl |
| 57 | as for I** | Br | C—H | $CF_3$ | cyclopropyl |
| 58 | as for I** | Br | C—H | $CF_3$ | $CF_3CH_2$— |
| 59 | as for I** | Br | C—H | $CF_3$ | cyclopropyl-$CH_2$— |
| 60 | as for I** | Br | C—H | $CF_3$ | isopropyl |

TABLE C

Compounds of formula Ic (Ic)

| Comp No. | Stereochemistry at * | X1 | X2 | X3 | R⁹ |
|---|---|---|---|---|---|
| 1 | racemic mixture | Cl | C—Cl | Cl | methyl |
| 2 | racemic mixture | Cl | C—Cl | Cl | ethyl |
| 3 | racemic mixture | Cl | C—Cl | Cl | cyclopropyl |
| 4 | racemic mixture | Cl | C—Cl | Cl | $CF_3CH_2$— |
| 5 | racemic mixture | Cl | C—Cl | Cl | cyclopropyl-$CH_2$— |
| 6 | racemic mixture | Cl | C—Cl | Cl | isopropyl |
| 7 | racemic mixture | Cl | C—H | Cl | methyl |
| 8 | racemic mixture | Cl | C—H | Cl | ethyl |
| 9 | racemic mixture | Cl | C—H | Cl | cyclopropyl |
| 10 | racemic mixture | Cl | C—H | Cl | $CF_3CH_2$— |
| 11 | racemic mixture | Cl | C—H | Cl | cyclopropyl-$CH_2$— |
| 12 | racemic mixture | Cl | C—H | Cl | isopropyl |
| 13 | racemic mixture | $CF_3$ | C—H | $CF_3$ | methyl |
| 14 | racemic mixture | $CF_3$ | C—H | $CF_3$ | ethyl |
| 15 | racemic mixture | $CF_3$ | C—H | $CF_3$ | cyclopropyl |
| 16 | racemic mixture | $CF_3$ | C—H | $CF_3$ | $CF_3CH_2$— |
| 17 | racemic mixture | $CF_3$ | C—H | $CF_3$ | cyclopropyl-$CH_2$— |
| 18 | racemic mixture | $CF_3$ | C—H | $CF_3$ | isopropyl |
| 19 | racemic mixture | Cl | C—H | $CF_3$ | methyl |
| 20 | racemic mixture | Cl | C—H | $CF_3$ | ethyl |
| 21 | racemic mixture | Cl | C—H | $CF_3$ | cyclopropyl |
| 22 | racemic mixture | Cl | C—H | $CF_3$ | $CF_3CH_2$— |
| 23 | racemic mixture | Cl | C—H | $CF_3$ | cyclopropyl-$CH_2$— |
| 24 | racemic mixture | Cl | C—H | $CF_3$ | isopropyl |
| 25 | racemic mixture | Br | C—H | $CF_3$ | methyl |
| 26 | racemic mixture | Br | C—H | $CF_3$ | ethyl |
| 27 | racemic mixture | Br | C—H | $CF_3$ | cyclopropyl |
| 28 | racemic mixture | Br | C—H | $CF_3$ | $CF_3CH_2$— |
| 29 | racemic mixture | Br | C—H | $CF_3$ | cyclopropyl-$CH_2$— |
| 30 | racemic mixture | Br | C—H | $CF_3$ | isopropyl |
| 31 | as for I** | Cl | C—Cl | Cl | methyl |
| 32 | as for I** | Cl | C—Cl | Cl | ethyl |
| 33 | as for I** | Cl | C—Cl | Cl | cyclopropyl |
| 34 | as for I** | Cl | C—Cl | Cl | $CF_3CH_2$— |
| 35 | as for I** | Cl | C—Cl | Cl | cyclopropyl-$CH_2$— |
| 36 | as for I** | Cl | C—Cl | Cl | isopropyl |
| 37 | as for I** | Cl | C—H | Cl | methyl |
| 38 | as for I** | Cl | C—H | Cl | ethyl |
| 39 | as for I** | Cl | C—H | Cl | cyclopropyl |
| 40 | as for I** | Cl | C—H | Cl | $CF_3CH_2$— |
| 41 | as for I** | Cl | C—H | Cl | cyclopropyl-$CH_2$— |
| 42 | as for I** | Cl | C—H | Cl | isopropyl |
| 43 | as for I** | $CF_3$ | C—H | $CF_3$ | methyl |
| 44 | as for I** | $CF_3$ | C—H | $CF_3$ | ethyl |
| 45 | as for I** | $CF_3$ | C—H | $CF_3$ | cyclopropyl |
| 46 | as for I** | $CF_3$ | C—H | $CF_3$ | $CF_3CH_2$— |
| 47 | as for I** | $CF_3$ | C—H | $CF_3$ | cyclopropyl-$CH_2$— |
| 48 | as for I** | $CF_3$ | C—H | $CF_3$ | isopropyl |
| 49 | as for I** | Cl | C—H | $CF_3$ | methyl |
| 50 | as for I** | Cl | C—H | $CF_3$ | ethyl |
| 51 | as for I** | Cl | C—H | $CF_3$ | cyclopropyl |
| 52 | as for I** | Cl | C—H | $CF_3$ | $CF_3CH_2$— |
| 53 | as for I** | Cl | C—H | $CF_3$ | cyclopropyl-$CH_2$— |
| 54 | as for I** | Cl | C—H | $CF_3$ | isopropyl |
| 55 | as for I** | Br | C—H | $CF_3$ | methyl |
| 56 | as for I** | Br | C—H | $CF_3$ | ethyl |
| 57 | as for I** | Br | C—H | $CF_3$ | cyclopropyl |
| 58 | as for I** | Br | C—H | $CF_3$ | $CF_3CH_2$— |
| 59 | as for I** | Br | C—H | $CF_3$ | cyclopropyl-$CH_2$— |
| 60 | as for I** | Br | C—H | $CF_3$ | isopropyl |

Compounds from Table C are preferred.

In one embodiment of the invention component B is an insecticidal compound selected from the group consisting of neonicotinoids, tetramic acids and tetronic acids, pyrethroids, diamides, carbamates, ethiprole, flupyradifurone, fipronil and -4-[[(6-Chloropyridin-3-yl)methyl](2,2-difluoroethyl)amino]furan-2(5H)-one.

In a further embodiment of the invention component B is an insecticidal compound selected from the group consisting of neonicotinoids, tetramic acids, pyrethroids, diamides and -4-[[(6-Chloropyridin-3-yl)methyl](2,2-difluoroethyl)amino]furan-2(5H)-one.

In a further embodiment of the invention component B is an insecticidal compound selected from the group consisting of neonicotinoids, tetramic acids, and pyrethroids.

In a further embodiment of the invention component B is an insecticidal compound selected from the group consisting of imidacloprid thiacloprid, spirotetramat, spiromesifen, spirodiclofen, flubendiamide, ethiprole, flupyradifurone, thiodicarb, deltamethrin, beta-cyfluthrin, aldicarb, fipronil, 4-[[(6-Chloropyridin-3-yl)methyl](2,2-difluoroethyl)amino]furan-2(5H)-one, lambda-cyhalothrin, and thiamethoxam.

In a further embodiment of the invention component B is an insecticidal compound selected from the group consisting of imidacloprid, thiacloprid, spirotetramat, spirodiclofen, flubendiamide, deltamethrin, beta-cyfluthrin, 4-[[(6-Chloropyridin-3-yl)methyl](2,2-difluoroethyl)amino]furan-2(5H)-one, lambda-cyhalothrin, and thiamethoxam In one embodiment of the invention component B is an insecticidal compound selected from the group consisting of
  pymetrozine;
  an organophosphate selected from the group consisting of sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate and diazinon;
  a pyrethroid selected from the group consisting of permethrin, cypermethrin, fenvalerate, esfenvalerate, deltamethrin, cyhalothrin, lambda-cyhalothrin, gamma-cyhalothrin, bifenthrin, fenpropathrin, cyfluthrin (including beta cyfluthrin), tefluthrin, ethofenprox, natural pyrethrin, tetramethrin, S-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;
  a carbamate including those selected from the group consisting of pirimicarb, triazamate, cloethocarb, carbofuran, furathiocarb, ethiofencarb, aldicarb, thiofurox, carbosulfan, bendiocarb, fenobucarb, propoxur, methomyl, thiodicarb and oxamyl;
  a macrolide selected from the group consisting of abamectin, emamectin benzoate, ivermectin, milbemycin, spinosad, azadirachtin and spinetoram;
  a diamide selected from the group consisting of flubendiamide, chlorantraniliprole (Rynaxypyr®) and cyantraniliprole;
  a neonicotinoid compound selected from the group consisting of imidacloprid, thiacloprid, acetamiprid, nitenpyram, dinotefuran, thiamethoxam, clothianidin, nithiazine and flonicamid;
  a tetramic acid or tetronic acid selected from spirotetramat, spirodiclofen and spiromesifen;
  fipronil In one embodiment of the invention component B is a compound selected from the group consisting of abamectin, chlorpyrifos, cyantraniliprole, emamectin, lambda cyhalothrin, pymetrozine, spirotetramat, thiamethoxam, clothianidin, imidacloprid and chlorantraniliprole.

In one embodiment of the invention component B is a compound selected from the group consisting of abamectin, chlorpyrifos, cyantraniliprole, emamectin, lambda cyhalothrin, pymetrozine, spirotetramat, and thiamethoxam.

In one embodiment of the invention component B is a compound selected from the group consisting of abamectin, lambda cyhalothrin, spirotetramat and clothianidin. In one embodiment component B is abamectin. In one embodiment component B is lambda cyhalothrin. In one embodiment component B is spirotetramat. In one embodiment component B is clothianidin.

In a preferred embodiment of the invention component B is an insecticidal compound selected from the group consisting of
  a pyrethroid selected from the group consisting of permethrin, cypermethrin, fenvalerate, esfenvalerate, deltamethrin, cyhalothrin, lambda-cyhalothrin, gamma-cyhalothrin, bifenthrin, fenpropathrin, cyfluthrin (including beta cyfluthrin), tefluthrin, ethofenprox, natural pyrethrin, tetramethrin, S-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;
  a neonicotinoid compound selected from the group consisting of imidacloprid, thiacloprid, acetamiprid, nitenpyram, dinotefuran, thiamethoxam, clothianidin, nithiazine and flonicamid;
  a tetramic acid or tetronic acid selected from the group consisting of spirotetramat, spirodiclofen and spiromesifen.

In a preferred embodiment of the invention component B is a tetramic acid compound selected from spirotetramat and spirodiclofen, more preferably spirotetramat.

In a preferred embodiment of the invention component B is a pyrethroid selected from the group consisting of permethrin, cypermethrin, fenvalerate, esfenvalerate, deltamethrin, cyhalothrin, lambda-cyhalothrin, gamma-cyhalothrin, bifenthrin, fenpropathrin, cyfluthrin (including beta cyfluthrin), tefluthrin, ethofenprox, natural pyrethrin, tetramethrin, S-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate, more preferably deltamethrin.

In a preferred embodiment of the invention component B is a neonicotinoid compound selected from the group consisting of imidacloprid, thiacloprid, acetamiprid, nitenpyram, dinotefuran, thiamethoxam, clothianidin, nithiazine and flonicamid, more preferably imidacloprid.

In a preferred embodiment of the invention component B is spirotetramat.

In a preferred embodiment of the invention component B is deltamethrin.

In a preferred embodiment of the invention component B is imidacloprid.

In a very preferred embodiment of the invention component A is a preferred group of compounds as described above and component B is spirotetramat.

In a very preferred embodiment of the invention component A is a preferred group of compounds as described above and component B is deltamethrin.

In a very preferred embodiment of the invention component A is a preferred group of compounds as described above and component B is imidacloprid.

The invention also included the following combinations:

A mixture of a compound selected from Tables A, B and C and abamectin.
A mixture of a compound selected from Tables A, B and C and chlorpyrifos.
A mixture of a compound selected from Tables A, B and C and cyantraniliprole.
A mixture of a compound selected from Tables A, B and C and emamectin.
A mixture of a compound selected from Tables A, B and C and cyhalothrin.
A mixture of a compound selected from Tables A, B and C and lambda cyhalothrin.
A mixture of a compound selected from Tables A, B and C and gamma cyhalothrin.
A mixture of a compound selected from Tables A, B and C and pymetrozine.
A mixture of a compound selected from Tables A, B and C and spirotetramat.
A mixture of a compound selected from Tables A, B and C and thiamethoxam.
A mixture of a compound selected from Tables A, B and C and chlorantraniliprole.
A mixture of a compound selected from Tables A, B and C and profenofos.
A mixture of a compound selected from Tables A, B and C and acephate.
A mixture of a compound selected from Tables A, B and C and azinphos-methyl.
A mixture of a compound selected from Tables A, B and C and methamidophos.
A mixture of a compound selected from Tables A, B and C and spinosad.
A mixture of a compound selected from Tables A, B and C and spinetoram.
A mixture of a compound selected from Tables A, B and C and flonicamid.
A mixture of a compound selected from Tables A, B and C and indoxacarb.
A mixture of a compound selected from Tables A, B and C and spirodiclofen.
A mixture of a compound selected from Tables A, B and C and spiromesifen.
A mixture of a compound selected from Tables A, B and C and sulfoxaflor.
A mixture of a compound selected from Tables A, B and C and fipronil.
A mixture of a compound selected from Tables A, B and C and imidacloprid.
A mixture of a compound selected from Tables A, B and C and thiacloprid.
A mixture of a compound selected from Tables A, B and C and acetamiprid.
A mixture of a compound selected from Tables A, B and C and nitenpyram.
A mixture of a compound selected from Tables A, B and C and dinotefuran.
A mixture of a compound selected from Tables A, B and C and clothianidin.
A mixture of a compound selected from Tables A, B and C and nithiazine.
A mixture of a compound selected from Tables A, B and C and pyriproxyfen.
A mixture of a compound selected from Tables A, B and C and buprofezin.
A mixture of a compound selected from Tables A, B and C and pyrifluquinazon.
A mixture of a compound selected from Tables A, B and C thiamethoxam and cyantraniliprole.
A mixture of a compound selected from Tables A, B and C thiamethoxam and chlorantraniliprole.
A mixture of a compound selected from Tables A, B and C and sulfoxaflor.
A mixture of a compound selected from Tables A, B and C and Lufeneron.
A mixture of a compound selected from Tables A, B and C Diafenthiuron.
A mixture of a compound selected from Tables A, B and C and Flubendiamide.
A mixture of a compound selected from Tables A, B and C and Tefluthrin.
A mixture of a compound selected from Tables A, B and C and Fipronil.
A mixture of a compound selected from Tables A, B and C and Ethiprole.
A mixture of a compound selected from Tables A, B and C and Flupyradifurone.
A mixture of a compound selected from Tables A, B and C and Iprodione.
A mixture of a compound selected from Tables A, B and C and Thiodicarb
A mixture of a compound selected from Tables A, B and C and Deltamethrin
A mixture of a compound selected from Tables A, B and C and beta-Cyfluthrin
A mixture of a compound selected from Tables A, B and C and Aldicarb
A mixture of a compound selected from Tables A, B and C and -4-[[(6-Chloropyridin-3-yl)methyl](2,2-difluoroethyl)amino]furan-2(5H)-one.
A mixture of a compound selected from Tables A, B and C and imidacloprid and Beta-cyfluthrin.

The present invention also relates to a method of controlling insects, acarines, nematodes or molluscs which comprises applying to a pest, to a locus of a pest, or to a plant susceptible to attack by a pest a combination of components A and B; seeds comprising a mixture of components A and B; and a method comprising coating a seed with a mixture of components A and B.

The present invention also includes pesticidal mixtures comprising a component A and a component B in a synergistically effective amount; agricultural compositions comprising a mixture of component A and B in a synergistically effective amount; the use of a mixture of component A and B in a synergistically effective amount for combating animal pests; a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a mixture of component A and B in a synergistically effective amount; a method for protecting crops from attack or infestation by animal pests which comprises contacting a crop with a mixture of component A and B in a synergistically effective amount; a method for the protection of seeds from soil insects and of the seedlings' roots and shoots from soil and foliar insects comprising contacting the seeds before sowing and/or after pre-germination with a mixture of component A and B in a synergistically effective amount; seeds comprising, e.g. coated with, a mixture of component A and B in a synergistically effective amount; a method comprising coating a seed with a mixture of component A and B in a synergistically effective amount; a method of controlling insects, acarines, nematodes or molluscs which comprises applying to a pest, to a locus of a pest, or to a plant susceptible to attack by a pest a combination of components A and B in a synergistically effective amount. Mixtures of A and B will normally be applied in an insecticidally, acaricidally, nematicidally or molluscicidally effective amount. In application components A and B may be applied simultaneously or separately.

The mixtures of the present invention can be used to control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are herein collectively referred to as pests. The pests which may be controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The mixtures of the invention are particularly effective against insects, acarines and/or nematodes.

According to the invention "useful plants" typically comprise the following species of plants: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

Plants are also to be understood as being those which by the use of recombinant DNA techniques are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030,295) or Cry1A.105; or vegetative insecticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (corn producing Cry1Ab), Agrisure®RW (corn producing mCry3A), Agrisure® Viptera (corn hybrids producing Vip3Aa); Agrisure300GT (corn hybrids producing Cry1Ab and mCry3A); YieldGard® (corn hybrids producing the Cry1Ab protein), YieldGard® Plus (corn hybrids producing Cry1Ab and Cry3Bb1), Genuity® SmartStax® (corn hybrids with Cry1A.105, Cry2Ab2, Cry1F, Cry34/35, Cry3Bb); Herculex® I (corn hybrids producing Cry1Fa) and Herculex®RW (corn hybrids producing Cry34Ab1, Cry35Ab1 and the enzyme Phosphinothricin-N-Acetyltransferase [PAT]); NuCOTN®33B (cotton cultivars producing Cry1Ac), Bollgard®I (cotton cultivars producing Cry1Ac), Bollgard®II (cotton cultivars producing Cry1Ac and Cry2Ab2) and VIPCOT®(cotton cultivars producing a Vip3Aa).

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. kurstaki which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

Useful plants of elevated interest in connection with present invention are cereals; soybean; rice; oil seed rape; pome fruits; stone fruits; peanuts; coffee; tea; strawberries; turf; vines and vegetables, such as tomatoes, potatoes, cucurbits and lettuce.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds. Insecticides that are of particular interest for treating seeds include thiamethoxam, imidacloprid and clothianidin. Accordingly, in one embodiment component B is selected from thiamethoxam, imidacloprid and clothianidin.

A further aspect of the instant invention is a method of protecting natural substances of plant and/or animal origin, which have been taken from the natural life cycle, and/or their processed forms against attack of pests, which comprises applying to said natural substances of plant and/or animal origin or their processed forms a combination of components A and B in a synergistically effective amount.

According to the instant invention, the term "natural substances of plant origin, which have been taken from the natural life cycle" denotes plants or parts thereof which have been harvested from the natural life cycle and which are in the freshly harvested form. Examples of such natural substances of plant origin are stalks, leafs, tubers, seeds, fruits or grains. According to the instant invention, the term "processed form of a natural substance of plant origin" is understood to denote a form of a natural substance of plant origin that is the result of a modification process. Such modification processes can be used to transform the natural substance of plant origin in a more storable form of such a substance (a storage good). Examples of such modification processes are pre-drying, moistening, crushing, comminuting, grounding, compressing or roasting. Also falling under the definition of a processed form of a natural substance of plant origin is timber, whether in the form of crude timber, such as construction timber, electricity pylons and barriers, or in the form of finished articles, such as furniture or objects made from wood.

According to the instant invention, the term "natural substances of animal origin, which have been taken from the natural life cycle and/or their processed forms" is understood to denote material of animal origin such as skin, hides, leather, furs, hairs and the like.

A preferred embodiment is a method of protecting natural substances of plant origin, which have been taken from the natural life cycle, and/or their processed forms against attack of pests, which comprises applying to said natural substances of plant and/or animal origin or their processed forms a combination of components A and B in a synergistically effective amount.

A further preferred embodiment is a method of protecting fruits, preferably pomes, stone fruits, soft fruits and citrus fruits, which have been taken from the natural life cycle, and/or their processed forms, which comprises applying to said fruits and/or their processed forms a combination of components A and B in a synergistically effective amount.

The combinations according to the present invention are furthermore particularly effective against the following pests: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panony-* chus ulmi (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The mixtures of the invention may be used for pest control on various plants, including soybean, corn, sugarcane, alfalfa, brassicas, oilseed rape (e.g. canola), potatoes (including sweet potatoes), cotton, rice, coffee, citrus, almonds, fruiting vegetables (e.g. tomatoes, pepper, chili, eggplant, cucumber, squash etc.), tea, bulb vegetables (e.g. onion, leek etc.), grapes, pome fruit (e.g. apples, pears etc.), and stone fruit (e.g. pears, plums etc.).

The mixtures of the invention may be used on soybean to control, for example, *Elasmopalpus lignosellus, Diloboderus abderus, Diabrotica speciosa, Sternechus subsignatus, Formicidae, Agrotis ipsilon, Julus* sspp., *Anticarsia gemmatalis, Megascelis* ssp., *Procornitermes* ssp., *Gryllotalpidae, Nezara viridula, Piezodorus* spp., *Acrosternum* spp., *Neomegalotomus* spp., *Cerotoma trifurcata, Popillia japonica, Edessa* spp., *Liogenys fuscus, Euchistus heros*, stalk borer, *Scaptocoris castanea, phyllophaga* spp., *Pseudoplusia includens, Spodoptera* spp., *Bemisia tabaci, Agriotes* spp. The mixtures of the invention are preferably used on soybean to control *Diloboderus abderus, Diabrotica speciosa, Nezara viridula, Piezodorus* spp., *Acrosternum* spp., *Cerotoma trifurcata, Popillia japonica, Euchistus heros, phyllophaga* spp., *Agriotes* sp The mixtures of the invention may be used on corn to control, for example, *Euchistus heros, Dichelops furcatus, Diloboderus abderus, Elasmopalpus lignosellus, Spodoptera frugiperda, Nezara viridula, Cerotoma trifurcata, Popillia japonica, Agrotis ipsilon, Diabrotica speciosa, Heteroptera, Procornitermes* ssp., *Scaptocoris castanea, Formicidae, Julus* ssp., *Dalbulus maidis, Diabrotica virgifera, Mocis latipes, Bemisia tabaci, heliothis* spp., *Tetranychus* spp., *thrips* spp., *phyllophaga* spp., *scaptocoris* spp., *Liogenys fuscus, Spodoptera* spp., *Ostrinia* spp., *Sesamia* spp., *Agriotes* spp. The mixtures of the invention are preferably used on corn to control *Euchistus heros, Dichelops furcatus, Diloboderus abderus, Nezara viridula, Cerotoma trifurcata, Popillia japonica, Diabrotica speciosa, Diabrotica virgifera, Tetranychus* spp., *thrips* spp., *phyllophaga* spp., *scaptocoris* spp., *Agriotes* spp.

The mixtures of the invention may be used on sugar cane to control, for example, *Sphenophorus* spp., termites, *Mahanarva* spp. The mixtures of the invention are preferably used on sugar cane to control termites, *Mahanarva* spp.

The mixtures of the invention may be used on alfalfa to control, for example, *Hypera brunneipennis, Hypera postica, Colias eurytheme, Collops* spp., *Empoasca solana, Epitrix, Geocoris* spp., *Lygus hesperus, Lygus lineolaris, Spissistilus* spp., *Spodoptera* spp., *Trichoplusia ni*. The mixtures of the invention are preferably used on alfalfa to control *Hypera* brunneipennis, *Hypera postica, Empoasca solana, Epitrix, Lygus hesperus, Lygus lineolaris, Trichoplusia ni*.

The mixtures of the invention may be used on brassicas to control, for example, *Plutella xylostella, Pieris* spp., *Mamestra* spp., *Plusia* spp., *Trichoplusia ni, Phyllotreta* spp., *Spodoptera* spp., *Empoasca solana, thrips* spp., *Spodoptera* spp., *Delia* spp. The mixtures of the invention are preferably used on brassicas to control *Plutella xylostella Pieris* spp., *Plusia* spp., *Trichoplusia ni, Phyllotreta* spp., *thrips* sp The mixtures of the invention may be used on oil seed rape, e.g. canola, to control, for example, *Meligethes* spp., *Ceutorhynchus napi, Psylloides* spp.

The mixtures of the invention may be used on potatoes, including sweet potatoes, to control, for example, *Empoasca* spp., *Leptinotarsa* spp., *Diabrotica speciosa, Phthorimaea* spp., *Paratrioza* spp., *Maladera matrida, Agriotes* spp. The mixtures of the invention are preferably used on potatoes, including sweet potatoes, to control *Empoasca* spp., *Leptinotarsa* spp., *Diabrotica speciosa, Phthorimaea* spp., *Paratrioza* spp., *Agriotes* spp.

The mixtures of the invention may be used on cotton to control, for example, *Anthonomus grandis, Pectinophora* spp., *heliothis* spp., *Spodoptera* spp., *Tetranychus* spp., *Empoasca* spp., *thrips* spp., *Bemisia tabaci, Lygus* spp., *phyllophaga* spp., *Scaptocoris* spp.

The mixtures of the invention are preferably used on cotton to control *Anthonomus grandis, Tetranychus* spp., *Empoasca* spp., *thrips* spp., *Lygus* spp., *phyllophaga* spp., *Scaptocoris* spp.

The mixtures of the invention may be used on rice to control, for example, *Leptocorisa* spp., *Cnaphalocrosis* spp., *Chilo* spp., *Scirpophaga* spp., *Lissorhoptrus* spp., *Oebalus pugnax*.

The mixtures of the invention are preferably used on rice to control *Leptocorisa* spp., *Lissorhoptrus* spp., *Oebalus pugnax*.

The mixtures of the invention may be used on coffee to control, for example, *Hypothenemus Hampei, Perileucoptera Coffeella, Tetranychus* spp. The mixtures of the invention are preferably used on coffee to control *Hypothenemus Hampei, Perileucoptera Coffeella*.

The mixtures of the invention may be used on citrus to control, for example, *Panonychus citri, Phyllocoptruta oleivora, Brevipalpus* spp., *Diaphorina citri, Scirtothrips* spp., *thrips* spp., *Unaspis* spp., *Ceratitis capitata, Phyllocnistis* spp. The mixtures of the invention are preferably used on citrus to control *Panonychus citri, Phyllocoptruta oleivora, Brevipalpus* spp., *Diaphorina citri, Scirtothrips* spp., *thrips* spp., *Phyllocnistis* spp.

The mixtures of the invention may be used on almonds to control, for example, *Amyelois transitella, Tetranychus* spp.

The mixtures of the invention may be used on fruiting vegetable, including tomatoes, pepper, chili, eggplant, cucumber, squash etc, to control *thrips* spp., *Tetranychus* spp., *Polyphagotarsonemus* spp., *Aculops* spp., *Empoasca* spp., *Spodoptera* spp., *heliothis* spp., *Tuta absoluta, Liriomyza* spp., *Bemisia tabaci, Trialeurodes* spp., *Paratrioza* spp., *Frankliniella occidentalis, Frankliniella* spp., *Anthonomus* spp., *Phyllotreta* spp., *Amrasca* spp., *Epilachna* spp., *Halyomorpha* spp., *Scirtothrips* spp., *Leucinodes* spp., *Neoleucinodes* spp. The mixtures of the invention are preferably used on fruiting vegetable, including tomatoes, pepper, chili, eggplant, cucumber, squash etc, to control, for example, *thrips* spp., *Tetranychus* spp., *Polyphagotarsonemus* spp., *Aculops* spp., *Empoasca* spp., *Spodoptera* spp., *heliothis* spp., *Tuta absoluta*, *Liriomyza* spp., *Paratrioza* spp., *Frankliniella occidentalis, Frankliniella* spp., *Amrasca* spp., *Scirtothrips* spp., *Leucinodes* spp., *Neoleucinodes* spp.

The mixtures of the invention may be used on tea to control, for example, *Pseudaulacaspis* spp., *Empoasca* spp., *Scirtothrips* spp., *Caloptilia theivora*. The mixtures of the invention are preferably used on tea to control *Empoasca* spp., *Scirtothrips* spp.

The mixtures of the invention may be used on bulb vegetables, including onion, leek etc to control, for example, *thrips* spp., *Spodoptera* spp., *heliothis* spp. The mixtures of the invention are preferably used on bulb vegetables, including onion, leek etc to control *thrips* spp.

The mixtures of the invention may be used on grapes to control, for example, *Empoasca* spp., *Lobesia* spp., *Frankliniella* spp., *thrips* spp., *Tetranychus* spp., *Rhipiphorothrips Cruentatus, Eotetranychus Willamettei, Erythroneura Elegantula, Scaphoides* spp. The mixtures of the invention are preferably used on grapes to control *Frankliniella* spp., *thrips* spp., *Tetranychus* spp., *Rhipiphorothrips Cruentatus, Scaphoides* spp.

The mixtures of the invention may be used on pome fruit, including apples, pairs etc, to control, for example, *Cacopsylla* spp., *Psylla* spp., *Panonychus ulmi, Cydia pomonella*. The mixtures of the invention are preferably used on pome fruit, including apples, pairs etc, to control *Cacopsylla* spp., *Psylla* spp., *Panonychus ulmi*.

The mixtures of the invention may be used on stone fruit to control, for example, *Grapholita molesta, Scirtothrips* spp., *thrips* spp., *Frankliniella* spp., *Tetranychus* spp. The mixtures of the invention are preferably used on stone fruit to control *Scirtothrips* spp., *thrips* spp., *Frankliniella* spp., *Tetranychus* spp.

The amount of a combination of the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of pest to be controlled or the application time.

The mixtures comprising a compound of formula I, e.g. those selected from table A, and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from table A and the active ingredients as described above is not essential for working the present invention.

The synergistic activity of the combination is apparent from the fact that the pesticidal activity of the composition of A+B is greater than the sum of the pesticidal activities of A and B.

The method of the invention comprises applying to the useful plants, the locus thereof or propagation material thereof in admixture or separately, a synergistically effective aggregate amount of a component A and a component B.

Some of said combinations according to the invention have a systemic action and can be used as foliar, soil and seed treatment pesticides.

With the combinations according to the invention it is possible to inhibit or destroy the pests which occur in plants or in parts of plants (fruit, blossoms, leaves, stems, tubers, roots) in different useful plants, while at the same time the parts of plants which grow later are also protected from attack by pests.

The combinations of the present invention are of particular interest for controlling pests in various useful plants or their seeds, especially in field crops such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and cucurbits.

The combinations according to the invention are applied by treating the pests, the useful plants, the locus thereof, the propagation material thereof, the natural substances of plant and/or animal origin, which have been taken from the natural life cycle, and/or their processed forms, or the industrial materials threatened by pests, attack with a combination of components A and B in a synergistically effective amount.

The combinations according to the invention may be applied before or after infection or contamination of the useful plants, the propagation material thereof, the natural substances of plant and/or animal origin, which have been taken from the natural life cycle, and/or their processed forms, or the industrial materials by the pests.

The combinations according to the invention can be used for controlling, i.e. containing or destroying, pests of the abovementioned type which occur on useful plants in agriculture, in horticulture and in forests, or on organs of useful plants, such as fruits, flowers, foliage, stalks, tubers or roots, and in some cases even on organs of useful plants which are formed at a later point in time remain protected against these pests.

When applied to the useful plants the compound of formula I is generally applied at a rate of 1 to 500 g a.i./ha in association with 1 to 2000 g a.i./ha, of a compound of component B, depending on the class of chemical employed as component B.

Generally for plant propagation material, such as seed treatment, application rates can vary from 0.001 to 10 g/kg of seeds of active ingredients. When the combinations of the present invention are used for treating seed, rates of 0.001 to 5 g of a compound of formula I per kg of seed, preferably from 0.01 to 1 g per kg of seed, and 0.001 to 5 g of a compound of component B, per kg of seed, preferably from 0.01 to 1 g per kg of seed, are generally sufficient.

The weight ratio of A to B may generally be between 1000:1 and 1:1000. In other embodiments that weight ratio of A to B may be between 500:1 to 1:500, for example between 100:1 to 1:100, for example between 1:50 to 50:1, for example 1:20 to 20:1, for example between 1:10 to 10:1 for example between 1:5 to 5:1. (The end points are included in the ranges.)

When component B is a tetramic acid such as spirotetramat the weight ratio of A to B may be for example 1.5:1 to 1:100, e.g. 1.5:1 to 1:70, e.g. 1:2 to 1:70. Preferably component A is a compound selected form the preferred groups of compounds above, more preferably compound C8. For example when component A is a compound of formula C8 and component B is spirotetramat the weight ratio of A:B may be 1.5:1 to 1:70.

When component B is a pyrethroid such as deltamethrin the weight ratio of A to B may be for example 10:1 to 1:100, e.g. 5:1 to 1:50, e.g. 2:1 to 1:30, e.g. 1.5:1 to 1:20, e.g. 1:1 to 1:20. Preferably component A is a compound selected form the preferred groups of compounds above, more preferably compound C8. For example when component A is a compound of formula C8 and component B is deltamethrin the weight ratio of A:B may be 2:1 to 1:30.

When component B is a neonicotinoid such as imidacloprid the weight ratio of A to B may be for example 100:1 to 1:100, e.g. 50:1 to 1:50, e.g. 10:1 to 1:10, e.g. 5:1 to 1:5. Preferably component A is a compound selected form the preferred groups of compounds above, more preferably compound C8. For example when component A is a compound of formula C8 and component B is imidacloprid the weight ratio of A:B may be 10:1 to 1:10.

The invention also provides pesticidal mixtures comprising a combination of components A and B as mentioned above in a synergistically effective amount, together with an agriculturally acceptable carrier, and optionally a surfactant.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules. A typical tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation. A typical pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula I together with a compound of component B, and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms the synergism factor SF corresponds to O/E. In the agricultural practice an SF of ≥1.2 indicates significant improvement over the purely complementary addition of activities (expected activity), while an SF of ≤0.9 in the practical application routine signals a loss of activity compared to the expected activity.

Tables 1 and 2 show mixtures of the present invention demonstrating notable synergistic effects. As the percent of mortality cannot exceed 100 percent, the unexpected increase in insecticidal activity can be greatest only when the separate active ingredient components alone are at application rates providing considerably less than 100 percent control. Synergy may not be evident at low application rates where the individual active ingredient components alone have little activity. However, in some instances high activity was observed for combinations wherein individual active ingredient alone at the same application rate had essentially no activity. The synergism is remarkable.

*Tetranychus urticae* (Two-Spotted Spider Mite)

Bean leaf discs on agar in 24-well microtiter plates are sprayed with test solutions (DMSO). After drying, the leaf discs are infested with mite populations of mixed ages. 8 days later, discs are checked for mobile stages (I removed "mixed population") mortality.

TABLE 1

|  | Application ppm | C8 + SPAT oberved control % | C8 observed control % | SPAT observed control % | expected control % | difference |
|---|---|---|---|---|---|---|
| C8 + SPAT | 1.5 + 6.25 | 90 | 65 | 25 | 73.75 | +16.25 |
| C8 + SPAT | 0.75 + 3.125 | 65 | 25 | 0 | 25 | +40 |
| C8 + SPAT | 0.375 + 1.56 | 25 | 0 | 0 | 0 | +25 |
| C8 + SPAT | 1.5 + 12.5 | 90 | 65 | 65 | 87.75 | +2.25 |
| C8 + SPAT | 0.75 + 6.25 | 75 | 25 | 25 | 43.75 | +31.25 |
| C8 + SPAT | 0.375 + 3.125 | 15 | 0 | 0 | 0 | +15 |
| C8 + SPAT | 1.5 + 25 | 95 | 65 | 80 | 93 | +2 |
| C8 + SPAT | 0.75 + 12.5 | 90 | 25 | 65 | 73.75 | +16.25 |
| C8 + SPAT | 0.375 + 6.25 | 25 | 0 | 25 | 25 | 0 |
| C8 + SPAT | 1.5 + 50 | 95 | 65 | 85 | 94.75 | +0.25 |
| C8 + SPAT | 0.75 + 25 | 90 | 25 | 80 | 85 | +5 |
| C8 + SPAT | 0.375 + 12.5 | 70 | 0 | 65 | 65 | +5 |
| C8 + SPAT | 0.187 + 6.25 | 70 | 0 | 25 | 25 | +45 |
| C8 + SPAT | 0.094 + 3.25 | 25 | 0 | 0 | 0 | +25 |
| C8 + SPAT | 1.5 + 100 | 100 | 65 | 85 | 94.75 | +5.25 |
| C8 + SPAT | 0.75 + 50 | 85 | 25 | 85 | 88.75 | −3.75 |
| C8 + SPAT | 0.375 + .25 | 90 | 0 | 80 | 80 | +10 |
| C8 + SPAT | 0.187 + 12.5 | 85 | 0 | 65 | 65 | +20 |
| C8 + SPAT | 0.094 + 6.25 | 25 | 0 | 25 | 25 | 0 |

TABLE 2

|  | Application ppm | C8 + DMET oberved control % | C8 observed control % | DMET observed control % | expected control % | difference |
|---|---|---|---|---|---|---|
| C8 + DMET | 6.0 + 6.25 | 100 | 95 | 75 | 98.75 | +1.25 |
| C8 + DMET | 3.0 + 3.125 | 100 | 95 | 0 | 95 | +5 |
| C8 + DMET | 1.5 + 1.562 | 100 | 80 | 0 | 80 | +20 |
| C8 + DMET | 0.75 + 0.781 | 90 | 55 | 0 | 55 | +35 |
| C8 + DMET | 0.375 + 0.39 | 40 | 0 | 0 | 0 | +40 |
| C8 + DMET | 6.0 + 12.5 | 100 | 95 | 80 | 99 | +1 |
| C8 + DMET | 3.0 + 6.25 | 100 | 95 | 75 | 98.75 | +1.25 |
| C8 + DMET | 1.5 + 3.125 | 75 | 80 | 0 | 80 | −5 |
| C8 + DMET | 0.75 + 1.562 | 70 | 55 | 0 | 55 | +15 |
| C8 + DMET | 0.375 + 0.781 | 15 | 0 | 0 | 0 | +15 |
| C8 + DMET | 3.0 + 12.5 | 100 | 95 | 80 | 99 | +1 |
| C8 + DMET | 1.5 + 6.25 | 100 | 80 | 75 | 95 | +5 |
| C8 + DMET | 0.75 + 3.125 | 65 | 55 | 0 | 55 | +10 |
| C8 + DMET | 3.0 + 25 | 100 | 95 | 90 | 99.5 | +0.5 |
| C8 + DMET | 1.5 + 12.5 | 100 | 80 | 80 | 96 | +4 |
| C8 + DMET | 0.75 + 6.25 | 90 | 55 | 75 | 88.75 | +1.25 |
| C8 + DMET | 0.375 + 3.125 | 25 | 0 | 0 | 0 | +25 |
| C8 + DMET | 3.0 + 50 | 100 | 95 | 90 | 99.5 | +0.5 |
| C8 + DMET | 1.5 + 25 | 100 | 80 | 90 | 98 | +2 |
| C8 + DMET | 0.75 + 12.5 | 90 | 55 | 80 | 91 | −1 |
| C8 + DMET | 0.375 + 6.25 | 40 | 0 | 75 | 75 | −35 |

In the above tables column 2 shows the application rates used, where the first rate given corresponds to the compound in column 4 and the second rate given corresponds to the compound in column 5. Columns 4 and 5 show the control observed from the compounds alone. Column 3 shows the control observed from the combined application of both compounds. Data is not shown for experiments where there was no insect mortality when the compounds were applied alone and in combination, or where one compound alone and the combination both resulted in complete mortality. When a compound applied alone gave no control at a particular rate, it is assumed that lower rates of that compound alone also give no control. DMET=deltamethrin, SPAT=spirotetramat, C8=compound 8 in Table C.

The invention claimed is:
1. A pesticidal mixture comprising a component A and a component B, wherein component A is a mixture enriched for the compound of formula I**

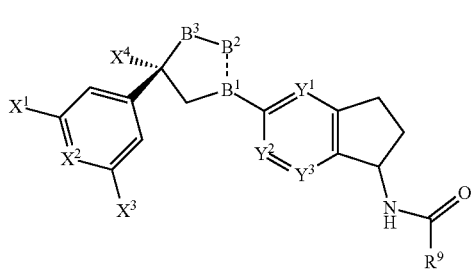

relative to the compound of formula I*

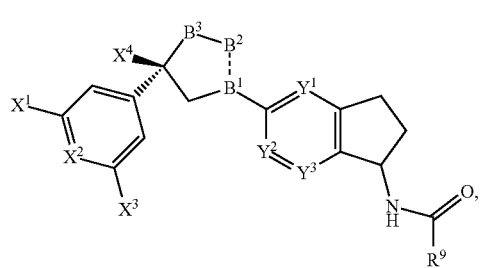

wherein
—$B^1$—$B^2$—$B^3$— is —C=N—O—, —C=N—$CH_2$— or —N—$CH_2$—$CH_2$—;
$Y^1$, $Y^2$ and $Y^3$ are independently CH or nitrogen; wherein no more than two of $Y^1$, $Y^2$ and $Y^3$ are nitrogen and wherein $Y^2$ and $Y^3$ are not both nitrogen;
$R^9$ is $C_1$-$C_4$alkyl, $C_1$-$C_4$haloalkyl, $C_1$-$C_4$alkyl-O—$CH_2$—, $C_1$-$C_4$haloalkyl-O—$CH_2$—, $C_3$-$C_6$cycloalkyl, $C_3$-$C_6$cycloalkyl-$CH_2$—, $C_1$-$C_4$alkyl-S—$CH_2$—, $C_1$-$C_4$alkyl-S(O)—$CH_2$—, or $C_1$-$C_4$alkyl-S($O_2$)—$CH_2$;
$X^2$ is C—$X^6$ or nitrogen;
$X^1$, $X^3$ and $X^6$ are independently hydrogen, halogen or trihalomethyl, wherein at least two of $X^1$, $X^3$ and $X^6$ are not hydrogen;
$X^4$ is trifluoromethyl, difluoromethyl or chlorodifluoromethyl;
and component B is a compound selected from a) a pyrethroid including those selected from the group consisting of permethrin, cypermethrin, fenvalerate, esfenvalerate, deltamethrin, cyhalothrin, lambda-cyhalothrin, gamma-cyhalothrin, bifenthrin, fenpropathrin, cyfluthrin (including beta cyfluthrin), tefluthrin, ethofenprox, natural pyrethrin, tetramethrin, S-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;
b) an organophosphate including those selected from the group consisting of sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate and diazinon;
c) a carbamate including those selected from the group consisting of pirimicarb, triazamate, cloethocarb, carbofuran, furathiocarb, ethiofencarb, aldicarb, thiofurox, carbosulfan, bendiocarb, fenobucarb, propoxur, methomyl, thiodicarb and oxamyl;
d) a benzoyl urea including those selected from the group consisting of diflubenzuron, triflumuron, hexaflumuron, flufenoxuron, lufenuron and chlorfluazuron;
e) an organic tin compound selected from the group consisting of cyhexatin, fenbutatin oxide and azocyclotin;
f) a pyrazole including those selected from the group consisting of tebufenpyrad and fenpyroximate;
g) a macrolide including those selected from the group consisting of abamectin, emamectin, ivermectin, milbemycin, spinosad, azadirachtin and spinetoram;
h) an organochlorine compound including those selected from the group consisting of endosulfan, benzene hexachloride, DDT, chlordane and dieldrin;
i) an amidine including those selected from the group consisting of chlordimeform and amitraz;
j) a fumigant agent including those selected from the group consisting of chloropicrin, dichloropropane, methyl bromide and metam;
k) a neonicotinoid compound including those selected from the group consisting of imidacloprid, thiacloprid, acetamiprid, nitenpyram, dinotefuran, thiamethoxam, clothianidin, nithiazine and flonicamid;
l) a diacylhydrazine including those selected from the group consisting of tebufenozide, chromafenozide and methoxyfenozide;
m) a diphenyl ether including those selected from the group consisting of diofenolan and pyriproxyfen;
n) indoxacarb;
o) chlorfenapyr;
p) pymetrozine;
q) a tetramic acid compound including those selected from the group consisting of spirotetramat and spirodiclofen, or a tetronic acid compound including spiromesifen;
r) a diamide including those selected from the group consisting of flubendiamide, chlorantraniliprole and cyantraniliprole;
s) sulfoxaflor;
t) metaflumizone;
u) fipronil and ethiprole;
v) pyrifluqinazon;
w) buprofezin;

x) diafenthiuron;
y) 4-[(6-Chloro-pyridin-3-ylmethyl)-(2,2-difluoro-ethyl)-amino]-5H-furan-2-one; and
z) flupyradifurone.

2. A pesticidal mixture according to claim 1, wherein —$B^1$—$B^2$—$B^3$— is —C=N—O—.

3. A pesticidal mixture according to claim 1, wherein $R^9$ is $C_1$-$C_4$alkyl, $C_1$-$C_4$haloalkyl or $C_3$-$C_4$cycloalkyl.

4. A pesticidal mixture according to claim 1, wherein $Y^1$ is CH, $Y^2$ is CH, and $Y^3$ is CH.

5. A pesticidal mixture according to claim 1, wherein $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro, or $X^1$ is chloro, $X^2$ is CH, $X^3$ is trifluoromethyl, or $X^1$ is chloro, $X^2$ is C—F, $X^3$ is chloro.

6. A pesticidal mixture according to claim 1, wherein —$B^1$—$B^2$—$B^3$— is —C=N—O—, $X^2$ is C—$X^6$, $Y^1$, $Y^2$, and $Y^3$ are CH and $R^9$ is $C_1$-$C_4$alkyl, $C_1$-$C_4$haloalkyl or $C_3$-$C_4$cycloalkyl.

7. A pesticidal mixture according to claim 1, wherein —$B^1$—$B^2$—$B^3$— is —C=N—O—, $X^2$ is C—$X^6$, $Y^1$, $Y^2$, and $Y^3$ are CH and $R^9$ is ethyl, —$CH_2CF_3$ or cyclopropyl.

8. A pesticidal mixture according to claim 1, wherein —$B^1$—$B^2$—$B^3$— is —C=N—O—, $Y^1$, $Y^2$, and $Y^3$ are CH and $R^9$ is ethyl, —$CH_2CF_3$ or cyclopropyl, $X^1$ is chloro, $X^2$ is CH, $X^3$ is chloro or $X^1$ is trifluoromethyl, $X^2$ is CH, $X^3$ is trifluoromethyl or $X^1$ is chloro, $X^2$ is C—Cl, $X^3$ is chloro, or $X^1$ is chloro, $X^2$ is CH, $X^3$ is trifluoromethyl, or $X^1$ is chloro, $X^2$ is C—F, $X^3$ is chloro.

9. A pesticidal mixture according to claim 1, wherein —$B^1$—$B^2$—$B^3$— is —C=N—O—, $Y^1$, $Y^2$, and $Y^3$ are CH, $R^9$ is ethyl, $X^1$ is chloro, $X^2$ is CH, $X^3$ is chloro and $X^4$ is trifluoromethyl.

10. A pesticidal mixture according to claim 1, wherein component B is a pyrethroid selected from the group consisting of permethrin, cypermethrin, fenvalerate, esfenvalerate, deltamethrin, cyhalothrin, lambda-cyhalothrin, gamma-cyhalothrin, bifenthrin, fenpropathrin, cyfluthrin, tefluthrin, ethofenprox, natural pyrethrin, tetramethrin, S-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;

a neonicotinoid compound selected from the group consisting of imidacloprid, thiacloprid, acetamiprid, nitenpyram, dinotefuran, thiamethoxam, clothianidin, nithiazine and flonicamid;

a tetramic acid or tetronic acid selected from the group consisting of spirotetramat, spirodiclofen and spiromesifen.

11. A pesticidal mixture according to claim 1, wherein component B is deltamethrin, spirotetramat or imidacloprid.

12. A pesticidal mixture according to claim 6, wherein component B is spirotetramat.

13. A pesticidal mixture according to claim 6, wherein component B is deltamethrin.

14. A pesticidal mixture according to claim 6, wherein component B is imidacloprid.

15. A pesticidal mixture according to claim 9, wherein component B is spirotetramat.

16. A pesticidal mixture according to claim 9, wherein component B is deltamethrin.

17. A pesticidal mixture according to claim 9, wherein component B is imidacloprid.

18. A pesticidal mixture according to claim 1, wherein the weight ratio of A to B is 1000:1 to 1:1000.

19. A pesticidal mixture according to claim 1, wherein the weight ratio of A to B is 100:1 to 1:100.

20. A method of controlling insects, acarines, nematodes or molluscs which comprises applying to a pest, to a locus of a pest, or to a plant susceptible to attack by a pest a combination of components A and B, wherein components A and B are as defined in claim 1.

21. A pesticidal mixture according to claim 1, wherein component A is at least 90% enriched for the compound of formula I**.

* * * * *